(12) United States Patent
Heidrich et al.

(10) Patent No.: US 8,857,242 B2
(45) Date of Patent: Oct. 14, 2014

(54) PHOTOACOUSTIC GAS SENSOR AND ITS USE

(75) Inventors: Helmut Heidrich, Berlin (DE); Peter Lutzow, Berlin (DE); Wolfgang Schlaak, Berlin (DE); Herbert Venghaus, Berlin (DE); Thomas Wegner, Altenbach (DE)

(73) Assignees: Miopas GmbH (DE); Fraunhofer-Gesellschaft zur Förderung der angewandten Forschung e.V. (DE)

( * ) Notice: Subject to any disclaimer, the term of this patent is extended or adjusted under 35 U.S.C. 154(b) by 795 days.

(21) Appl. No.: 13/063,740

(22) PCT Filed: Sep. 9, 2009

(86) PCT No.: PCT/EP2009/006743
§ 371 (c)(1),
(2), (4) Date: Jun. 1, 2011

(87) PCT Pub. No.: WO2010/028865
PCT Pub. Date: Mar. 18, 2010

(65) Prior Publication Data
US 2011/0290002 A1    Dec. 1, 2011

(30) Foreign Application Priority Data

Sep. 12, 2008 (DE) .......................... 10 2008 047 658

(51) Int. Cl.
*G01N 21/27* (2006.01)
*G01N 29/036* (2006.01)
*G01N 21/17* (2006.01)
*G01N 29/24* (2006.01)

(52) U.S. Cl.
CPC .......... *G01N 21/1702* (2013.01); *G01N 29/036* (2013.01); *G01N 2291/0215* (2013.01); *G01N 29/2418* (2013.01); *G01N 2021/1704* (2013.01)
USPC ...................................... 73/24.02

(58) Field of Classification Search
CPC .......... G01N 21/1702; G01N 29/2418; G01N 2021/1704; G01N 2291/0215
USPC ...................................... 73/24.02
See application file for complete search history.

(56) References Cited

U.S. PATENT DOCUMENTS 5,886,249 A   3/1999   Bonne
6,061,481 A *   5/2000   Heidrich et al. ................ 385/14

(Continued)

FOREIGN PATENT DOCUMENTS

CH      686589 A5    4/1996
DE     69610225 T2    1/2001

(Continued)

OTHER PUBLICATIONS

"International Application No. PCT/EP2009/006743, International Search Report and Written Opinion mailed Jan. 22, 2010", 10 pgs.

(Continued)

*Primary Examiner* — Daniel S Larkin
(74) *Attorney, Agent, or Firm* — Schwegman Lundberg & Woessner, P.A.

(57) ABSTRACT

The invention relates to a gas sensor having a mechanical microresonator, which has an excitation apparatus for optically exciting a mechanical oscillation of the microresonator as well as a reading apparatus for detecting the oscillation of the microresonator, wherein the reading apparatus comprises a waveguide which is implemented together with the microresonator on a dielectric or semiconducting substrate and is intended to optically read the oscillation of the microresonator, and wherein the excitation apparatus has an optical waveguide which is implemented on the same substrate and optically connects an excitation light source to the immediate surroundings of the microresonator. The invention also relates to a use of such a sensor to analyse a gas composition.

15 Claims, 4 Drawing Sheets

(56) References Cited

U.S. PATENT DOCUMENTS 6,082,178 A 7/2000 Bernstein et al.
7,304,732 B1 12/2007 Polcawich et al.

FOREIGN PATENT DOCUMENTS

| EP | 0979401 A1 | 2/2000 |
| WO | WO-03/104767 A2 | 12/2003 |

OTHER PUBLICATIONS

Breguet, J., et al., "Photoacoustic Detection of Trace Gases with an Optical Microphone", Sensors and Actuators A, vol. 48, No. 1 (1995) 29-35, (May 1, 1995), 29-35.

Firebaugh, Samara L., et al., "Miniaturization and Integration of Photoacoustic Detection", Journal of Applied Physics, vol. 92, No. 3, (Aug. 1, 2002), 1555-1563.

Firebaugh, Samara L., et al., "Miniaturization and Integration of Photoacoustic Detection with a Microfabricated Chemical Reactor System", Journal of Microelectromechanical Systems, vol. 10, No. 2, (Jun. 2001), 232-237.

Munir, Q., et al., "Fiberoptic Sensor in a Resonant Optoacoustic Cell", Optics Communications, vol. 52, No. 4, (Dec. 15, 1984), 269-273.

"International Application No. PCT/EP2009/006743, International Preliminary Report on Patentability mailed Mar. 24, 2011", (English Translation), 6 pgs.

\* cited by examiner

PHOTOACOUSTIC GAS SENSOR AND ITS USE

PRIORITY CLAIM TO RELATED APPLICATIONS

This application is a national stage application under 35 U.S.C. §371 of PCT/EP2009/006743, filed Sep. 9, 2009, and published as WO 2010/028865 A1 on Mar. 18, 2010, which claims priority to German Application No. 10 2008 047 658.7, filed Sep. 12, 2008, which applications and publication are incorporated herein by reference and made a part hereof in their entirety, and the benefit of priority of each of which is claimed herein.

FIELD OF THE INVENTION

The invention relates to a gas sensor with a mechanical microresonator, according to the introductory part of the main claim as well as to a use of such a sensor for a gas composition.

BACKGROUND OF THE INVENTION

A sensor of the known type comprises an excitation device for the optical excitation of a mechanical oscillation of the microresonator as well as a read-out device for detecting the oscillation of the microresonator. Such a sensor is known for example from the document WO 03/104767 A2. The sensor which is described there, may be used for the selective detection of gases, by way of a gas located in an environment of the microresonator being radiated with light of an absorption frequency of the gas, wherein this light is modulated with a resonant frequency of the microresonator. Thereby, the absorption frequency may correspond to an absorption spectral line of the gas, or, in the case of an upper-harmonic excitation, may correspond to an integer multiple of this. Absorption of this light by the gas then effects a pressure fluctuation with a time dependency corresponding to the resonant frequency of the microresonator, by which means the microresonator is excited into oscillation. Since thereby, an oscillation amplitude of the microprocessor depends significantly on whether and how greatly the gas in the environment of the microresonator absorbs light of the frequency or wavelength of the light used for the excitation, one may deduce a composition of the gas by way of a monitoring of an oscillation of the microresonator. With the state of the art from the mentioned document, the oscillation of the microresonator is detected by way of a piezovoltage produced by a movement of the microresonator being measured, thus the mechanical oscillation being converted into an electrical signal.

Disadvantageously, the described sensor therefore may not be applied in environments, in which an operation of electric apparatus may have harmful effects. This in particular concerns environments with strong electrical fields, explosive or easily ignitable media or environments which are sensitive for other reasons, for example in medical analysis arrangements.

SUMMARY OF THE INVENTION

It is therefore the objective of the invention, to develop a corresponding gas sensor which permits a gas composition to be analyzed in electrically sensitive environments. It is further the objective of the invention to suggest a method for the analysis of a gas composition, which may also be carried out in an accordingly sensitive environment.

According to the invention, this objective is achieved by a gas sensor with the features of the latter part of the main claim in combination with the features of the introductory part of the main claim as well as by using this sensor for analyzing a gas composition. Advantageous designs and further developments of the invention are to be deduced from the features of the dependent claims.

With the suggested gas sensor which is indicated hereinafter only as sensor, the read-out device comprises a waveguide for optically reading out the oscillation of the microresonator, the waveguide and the microresonator being arranged on a dielectric or semiconducting substrate, wherein the excitation device comprises a light waveguide which is arranged on the same substrate and which optically connects an excitation light source to a direct environment of the microresonator. The sensor therefore comprises planar-integrated optics or is formed by planar-integrated optics. Thereby, typically a semiconductor substrate is used as a substrate. Alternatively, the substrate may however also be formed of plastic, for example of Plexiglas or another polymer, or be formed from glass. By way of the fact that an optical waveguide is provided for reading out the oscillations of the microresonator, it is possible to optically read out the mechanical oscillation of the microresonator and thus without the use of electricity. This permits an application of the sensor also in environments, in which electric fields and a presence of electrical conductors must be avoided. Thereby, the waveguide provided for optical read-out of the oscillation, may under certain circumstances be identical to the light waveguide of the excitation device. Due to the fact that the waveguide of the read-out device, the microresonator and the light waveguide of the excitation device are arranged on a single substrate, not only does an advantageously compact construction of the sensor result, but additionally one prevents the sensor with the optical read-out device and the optical excitation device, from being prone to maladjustment, which renders the sensor robust and durable, and by which means an adjustment effort which would otherwise be necessary with comparable arrangements, is done away with.

The described sensor may be used in an advantageously simple manner for analyzing a gas composition, by way of a gas which is located in the environment of the resonator and which, in order to be analyzed, is being irradiated with—not necessarily visible—light of the excitation light source, such that the microresonator is set into an oscillation condition when a wavelength of this light corresponds to an absorption wavelength of the gas, wherein the oscillation condition is optically detected by way of the read-out device. A modulation frequency or pulse frequency of the light of a resonant frequency of the microresonator, said light being used for excitation, may be selected accordingly for this. Absorption wavelength does not only designate wavelengths which correspond to an absorption spectral line of the gas, but also in particular integer multiples or simple fractions thereof, which permit a higher-harmonic or sub-harmonic excitation. A spectral analysis of the gas is thus possible in an advantageous manner without electrical conductors in the environment of the gas and whilst avoiding external electrical fields.

With preferred embodiments of the invention, the substrate is formed by a semiconductor wafer or part of a semiconductor wafer. Then, the sensor or also a large number of corresponding sensors may be manufactured in a simple manner, by way of an optical blocking layer which is arranged on the semiconductor wafer and which may for example be formed from a silicon layer, and a waveguide layer arranged above the blocking layer, being structured by way of photolithography and etching, such that the lightwave guide of the excitation device and the waveguide of the read-out device are formed in the waveguide layer, wherein the blocking layer is removed at some locations, such that the microresonator is formed by an undercut structure. Thereby, the microresonator may be formed in the waveguide layer and/or in a further layer which is arranged between the waveguide layer and the blocking layer. The waveguide layer may be formed by a semiconductor layer arranged on the blocking layer and for example of silicon, and may also comprise a further layer for example of silicon nitrite, arranged on the blocking layer or on such a semiconductor layer. The waveguide layer in any case has a greater optical index than the optical blocking layer. The blocking layer may be removed by way of an etching means which is applied in a gaseous or vaporous manner and/or subsequently removed by way of supercritical drying, for forming the undercut structure in the environment of the microresonator. Thereby, in the present document, an optical buffer is included in the term blocking layer or optical blocking layer.

Thus advantageously, one obtains an advantageously simply realizable construction of the sensor, with which the microresonator and/or the light waveguide of the excitation device and/or of the waveguide of the read-out device are arranged in or on a suitably structured semiconductor layer or dielectric layer which is separated from the substrate by way of a blocking layer which is removed at locations, in particular below freely oscillating parts of the microresonator. Thereby, the semiconductor layer is typically formed by a silicon layer, whereas the blocking layer with preferred embodiments may be formed from $SiO_2$, in order to permit a manufacture of the sensor with proved and tested techniques. The substrate too may be formed from silicon or comprise a silicon layer with preferred embodiments.

The excitation light source may e.g. be a laser diode or another light-emitting diode, wherein a particularly compact construction of the sensor results when this diode too is arranged on the substrate. However with this, one has to forgo the omission of electric connections. Alternatively, the excitation light source may however also be connected to the light waveguide of the excitation device which is arranged on the substrate, e.g. by way of fibre coupling. The same may apply to a read-out light source which is encompassed by the read-out device and which may likewise be designed as a light-emitting diode, and to one or more light-sensitive elements of the read-out device. Also such light-sensitive elements may be arranged on the substrate or be fibre-coupled to the waveguide of the read-out device.

The excitation light source should—preferably by way of a control or regulation unit set up in a suitable manner with regard to programming technology—be able to be operated in a pulsed, wavelength-modulated or intensity-modulated manner with a pulse frequency or modulation frequency which corresponds to a resonant frequency of the microresonator or to a sub-harmonic or upper-harmonic excitation of the mechanical microresonator. With this, one may achieve a particularly clear dependence of an oscillation amplitude of the microresonator on an absorption frequency of the gas surrounding it. In order to permit a spectral analysis of a gas over an extended wavelength region, the excitation light source may be set up for emitting light of tunable wavelengths. An absorption spectrum of the gas surrounding the microresonator may then be recorded in a simple manner by way of measuring the oscillation amplitude of the microresonator in dependence on the wavelength of the excitation light source, whilst this wavelength is tuned with a modulation frequency or pulse frequency, which remains constant.

The mechanical microresonator may comprise one or two oscillation arms which may also be designated as cantilevers or tongues. Typically, the at least one oscillation arm thereby has a length of between 15 μm and 300 μm. The most favorable length thereby will be dependent on the width of the oscillation arm and be about 10 to 300 times this width. The thus formed mechanical microresonator may e.g. usefully have a resonant frequency of between 1 kHz and 1 MHz. If the microresonator has only one oscillation arm, the light waveguide of the excitation device may be led such that a light exit surface of this light waveguide is directed onto a space between the oscillation arm and a fixed wall, so that an excitation of the gas located there results in an oscillation of the oscillation arm. The microresonator may however also comprise two tuning-fork-like oscillation arms which oscillate to one another, wherein the light waveguide of the excitation device in this case is typically directed onto a space between the two oscillation arms, so that a radiation of the gas located there may excite an oscillation of the microresonator in an as efficient as possible manner.

The read-out device of the sensor may be designed such that the waveguide or a further waveguide of the read-out device extends over the oscillation arm or over at least one of the oscillation arms of the microresonator. For this, the at least one oscillation arm may either be designed completely as a waveguide or comprise a layer which forms the waveguide. By way of this, one succeeds in optical characteristics of the waveguide and thus of the read-out device changing with a movement of the microresonator, in order to permit a detection of the oscillation of the microresonator, in a simple manner with regard to design.

The waveguide or a further waveguide of the read-out device may in particular extend over the first oscillation arm and a second oscillation arm of the microresonator, such that a transmission of light from one end of the first oscillation arm to an end of the second oscillation arm is possible. For this, e.g. each of the oscillation arms may comprise a coupling-out surface or coupling-in surface, wherein these coupling surfaces are arranged lying opposite and parallel to one another. With such an arrangement e.g. one may use a change of an optical coupling between the ends of the oscillation arms and thus a change of the transmission between the oscillation arms in dependence on a movement of the oscillation arms caused by the oscillation, for detecting the oscillation.

The coupling surfaces at the ends of the two oscillation arms may also be designed in a part-reflecting manner, so that they form a Fabry-Perot resonator between the two oscillation arms. In this case, a change of the resonance characteristics of the thus formed Fabry Perot resonator which is caused by an oscillation of the oscillation arms, may be used for detecting the oscillation.

One may envisage the waveguide extending over the oscillation-capable oscillation arms of the microresonator being optically coupled to a further waveguide of the read-out device, for example via an optical four-port element such as a directional coupler, with which a coupling is effected by way of cross-talk in the evanescent field. Then, the waveguide extending over the oscillation arms may form an optical resonator, whose optical characteristics depend on the oscillation condition of the mechanical microresonator and which is excited into oscillation by way of the mentioned coupling effect.

With another embodiment, the waveguide of the read-out device may be arranged next to the oscillation arm or to at least one of the oscillation arms of the microresonator, such that light exiting from this waveguide after a reflection at the oscillation arm of the microresonator, may be coupled again into the waveguide. Since a phase of the light which is thus coupled again into the waveguide depends very sensitively on the specific position of the oscillation arm, in this manner one may detect an oscillation condition of the mechanical microresonator in a very accurate manner.

One may detect an oscillation of the mechanical microresonator in a particularly reliable manner if the read-out device comprises at least two waveguides which are arranged on the common substrate and which are optically coupled to one another, wherein one of the waveguides is coupled to the mechanical microresonator, wherein a read-out light source is arranged at an end of one of the two waveguides and wherein a light-sensitive element is arranged at another end of these two waveguides. Thereby, the read-out light source may be formed by a light-emitting diode which is preferably arranged on the same substrate, for example a laser diode, and the light-sensitive element as a detector preferably arranged on the same substrate, for example in the form of a photodiode. A coupling between the two waveguides may be achieved by way of cross-talk in the evanescent field, for example via an optical four-port element such as a directional coupler. The two waveguides may form a Michelson interferometer in this manner. A sampling of the oscillation condition of the microresonator may thus be effected in an interferometric manner. For this, a feeding waveguide coming from the read-out light source may, in parts, run parallel to a waveguide leading to the detector, so that the feeding waveguide may oscillate relative to the last mentioned waveguide and the magnitude of the signal coupled from one waveguide to the other depends on the oscillation condition of the microresonator.

The at least one waveguide of the read-out device may form a waveguide circuit which is preferably designed with single-mode technology, thus exclusively or at least partially with single-mode waveguides. The read-out light source should thus interact with the waveguide of the read-out device or with one of the waveguides of the read-out device such that light which is coupled from the read-out light source into the waveguide only encompasses a single spatial mode. The waveguides may be tapered on at the coupling surfaces, in order to permit a low-loss coupling-in or coupling-out of light. The coupling surfaces may also be anti-reflection coated for this.

BRIEF DESCRIPTION OF DRAWINGS

Embodiment examples of the invention are hereinafter described by way of the FIGS. 1 to 10. There are shown in FIG. 1 a plane view of a sensor in a first embodiment of the invention as well as thereunder, a cross section through this sensor at two different locations, FIG. 2 in a corresponding representation, a plane view of a sensor in a second embodiment of the invention as well as a cross section through a part of this sensor, FIG. 3 in a corresponding representation, a third embodiment example for a corresponding sensor, FIG. 4 a perspective view of a mechanical microresonator for use in a comparable sensor, FIG. 5 a representation of the microresonator from FIG. 4, which illustrates how this is excited into a mechanical oscillation, FIG. 6 in a corresponding representation, an alternative excitation of a mechanical oscillation of this microresonator, FIG. 7 a perspective representation of the same microresonator, in which it is illustrated how a mechanical oscillation of the microresonator is optically read out, FIG. 8 a perspective view of an alternatively designed microresonator for a corresponding sensor, FIG. 9 a corresponding representation of a microresonator for a corresponding sensor in a further modification, and FIG. 10 a perspective view of a microresonator for a sensor of the type formed in FIG. 1.

DESCRIPTION OF THE PREFERRED EMBODIMENT

Figure 1:
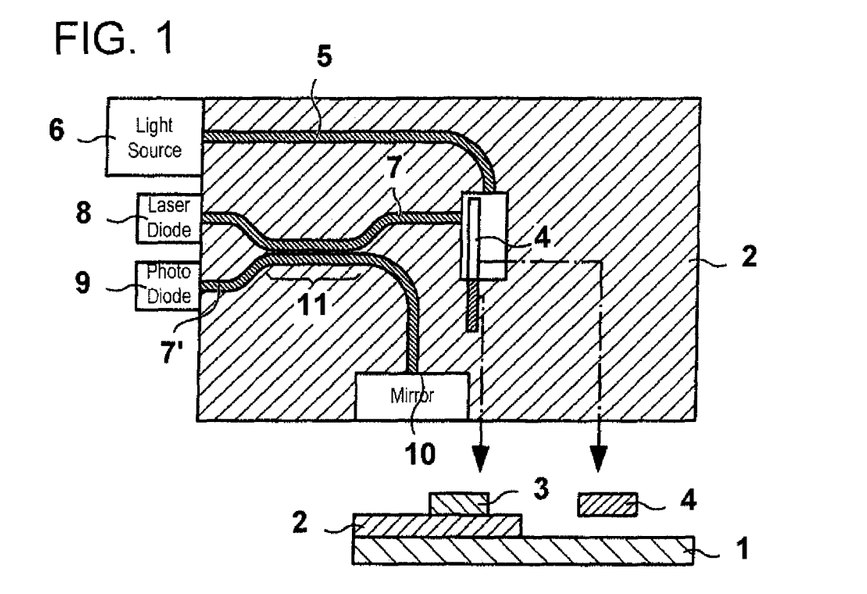

With regard to the sensor represented in FIG. 1, it is the case of a gas sensor which is constructed on the basis of a substrate 1 which has a thickness of about 0.5 mm and is formed by a part of a silicon wafer. A blocking layer 2 is arranged on this substrate 1 and has a thickness of about 2 μm and is formed from $SiO_2$. Left-over remains of a silicon layer 3 arranged initially over the blocking layer 2 and covering the whole surface, by way of a suitable structuring, form a mechanical microresonator which, in this embodiment, is an oscillation arm 4, a light waveguide 5 which connects an excitation light source 6 to a direct environment of the oscillation arm 4, as well as two optical waveguides 7 and 7' which serve for the optical reading-out of a mechanical oscillation of the microresonator. The blocking layer 2, which in the plane view of FIG. 1 is represented in a hatched manner, is removed in parts, in particular below the freely oscillating part of the oscillation arm 4. The excitation light source 6 is given by a laser diode and together with the light waveguide 5 forms an excitation device for the optical excitation of a mechanical oscillation of the microresonator. Under certain circumstances, this laser diode too, instead of which also another light-emitting diode may be used, may be arranged on the substrate 1. In order to be able to excite an oscillation of the oscillation arm 4, the excitation light source 6 is set up for emitting light of a tunable wavelength, wherein it may additionally be operated in a pulsed, wavelength-modulated or intensity-modulated manner, with a pulse frequency or modulation frequency which corresponds to the or one resonant frequency of the mechanical microresonator.

The waveguides 7 and 7' in combination with a laser diode 8 arranged at one end of the waveguide 7, a photodiode 9 arranged at one end of the other waveguide 7', with a mirror 10 arranged at an opposite end of the waveguide 7' and with a control unit which is not shown in FIG. 1, for activating the laser diode 8 and for evaluating a signal of the photodiode 9, form an interferometric read-out device, with which the mechanical oscillation of the microresonator may be detected. For this, the waveguide 7 is located close to the oscillation arm 4 of the microresonator such that light exiting from the waveguide 7, is coupled again into the waveguide 7 after a reflection at the oscillation arm 4. Moreover, the two waveguides 7 and 7' are coupled optically to one another by way of a directional coupler 11 which forms a four-port element, such that a cross-talk in the evanescent field of the two waveguides 7 and 7' is possible. For this, the waveguides 7 and 7' run parallel to each other at a small distance in the region of the directional coupler 11, so that correlated optical oscillations may form in the two waveguides 7 and 7', wherein a variable of a signal transmitting in the directional coupler 11 depends on the oscillation condition of the microresonator. The origin for this lies in the fact that an optical length of a measurement arm formed by the waveguide 7 depends on a state-of-motion or state-of-vibration of the oscillation arm 4. The read-out device forms an optical interferometer which apart from the mentioned measurement arm, comprises a reference arm which is formed by the waveguide 7'. By way of this, a scanning of the oscillation condition of the microresonator may be effected interferometrically with the described read-out device. One may also use another LED instead of the laser diode.

The part of the described gas sensor which is formed on the substrate 1 forms planar-integrated optics, wherein in particular the waveguides 7 and 7' are single-mode waveguides, thus are designed in a manner such that light coupled in the waveguides 7 and 7' from the laser diode 8 propagates with only one spatial mode.

In order, with the gas sensor shown in FIG. 1, to analyze a composition of a gas located in the environment of the microresonator, this environment is irradiated with an excitation light source 6 with light of a different wavelength, wherein this light in each case is modulated by pulses, wavelength modulation or intensity modulation with the resonant frequency of the mechanical microresonator. If the wavelength of this light corresponds to an absorption wavelength—possibly to a sub-harmonic or higher-harmonic excitation wavelength-of the gas, the oscillation arm 4 is excited to oscillate, since then the pressure in the environment of the oscillation arm 4 changes with the resonant frequency. The oscillation condition of the microresonator is thereby detected in the already described manner by way of the read-out device, so that a spectral analysis of the gas may be effected, without electrical leads in the environment of the gas.

The laser diode 8 and the photodiode 9 of the read-out device may also be arranged on the substrate 1, thus forming a monolithically integrated component of the optics on the substrate 1. With alternative embodiments, instead of the mentioned silicon wafer, one may also use another dielectric material for forming the substrate 1.

Figure 2:
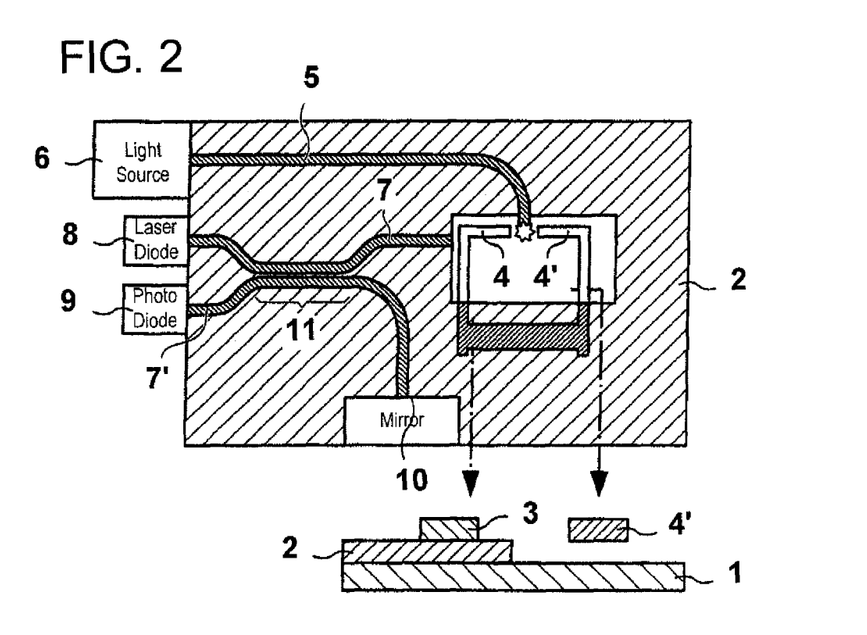

Another embodiment of a respective gas sensor is represented in FIG. 2. Recurring features thereby, as also in the following figures, are provided again with the same reference numerals, without once again being explained in detail. The gas sensor shown in FIG. 2 differs from the previously described embodiment example merely by way of the fact that the mechanical microresonator comprises two tuning-fork-like oscillation arms 4 and 4' oscillating towards one another. Thereby, the oscillation arms 4 and 4' are again dimensioned such that the microresonator has a resonant frequency of the same magnitude as with the previously described embodiment example. The light waveguide 5 of the excitation device in this case is directed onto a gap between the two oscillation arms 4 and 4', so that, with an operation of the excitation light source 6 in the previously described manner, e.g. the basic mode of the microresonator is excited, in which the oscillation arms 4 and 4' oscillate to one another. Instead of the fundamental mode, in a suitable manner, one may also excite another mode of the mechanical microresonator.

Figure 3:
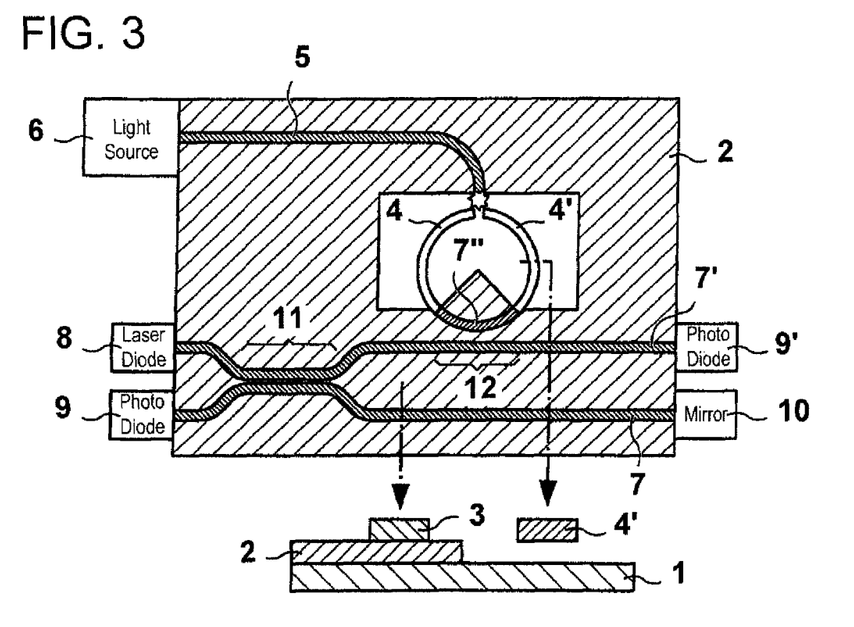

A further embodiment example of a similar gas sensor is shown in FIG. 3. Here too, the microresonator of the gas sensor comprises two tuning-fork-like oscillation arms 4 and 4' which oscillate towards each other, wherein the read-out device, differing from the previously described embodiment example, comprises a further waveguide 7" which extends over the two oscillation arms 4 and 4' of the microresonator, and forms an optical ring resonator. With the present embodiment example, the oscillation arms 4 and 4' are designed completely as waveguides for this. The optical ring resonator which is formed by the further waveguide 7" is coupled to the waveguide 7' by way of an additional directional coupler 12 and, by way of this, forms a part of the read-out device of this gas sensor. The oscillation arms 4 and 4' of the microresonator which here, as with the previously described embodiment example, may be excited into oscillation, end in two coupling surfaces which are arranged parallel to each other, so that light may be transmitted between the ends of the two oscillation arms 4 and 4'. The strength of the optical coupling which is thus realized between the ends of the two oscillation arms 4 and 4' thereby depends on a prevailing distance between these two ends and thus on an oscillation condition of the mechanical microresonator. Additionally, the two coupling surfaces may be designed in a part-reflecting manner at the ends of the oscillation arms 4 and 4', so that they form a Fabry-Perot resonator between the two oscillation arms 4 and 4', whose resonance characteristics change with deformation of the oscillation arms 4 and 4'. Such a change of the resonance characteristic of the mentioned Fabry-Perot resonator may in turn be read out in an optical manner, in order to detect the mechanical oscillation of the microresonator.

With the embodiment example from FIG. 3, an excitation of the oscillation of the microresonator designed as a micro-ring with the oscillation arms 4 and 4', is effected preferably again by an optical pulse excitation, by way of optical pulses being fed into the gap between the two oscillation arms 4 and 4', via the light waveguide 5, with a pulse repetition rate which corresponds to a mechanical resonant frequency of the microresonator. These pulses there, by way of frequency-selective absorption, bring the gas to be detected into oscillation, and lead to a greater resonance amplitude of the micro-ring. A deflection of the oscillation arms 4 and 4' of the microresonator, entailed by this, here is detected via a shift of the so-called free spectral range (FSR) or generally via a change of the resonance characteristic of the integrated-optical ring resonator formed by the microresonator. Due to the fact that the waveguide 7' of the read-out device formed by a detection waveguide circuit, is optically coupled on the micro-ring by way of the directional coupler 12, a resonant frequency shift of the optical ring resonator which is caused by a mechanical oscillation, may be detected as an amplitude change. For this, the read-out device in the present case, apart from the laser diode 8 which functions as a read-out light source, comprises two photodiodes 9 and 9' as well as a mirror 10, which in each case are connected to one end of one of the waveguides 7 or 7'. Thereby, also one of the photodiodes 9 or 9' may be replaced by a further reflecting element.

In the embodiment examples from the FIGS. 1 to 3, the excitation device as well as the read-out device are formed by way of a planar, integrated-optical waveguide circuit, wherein the waveguides 7 and 7' of the read-out device have a Michelson-Interferometer architecture. Thereby, the waveguides 7 and 7' define a spatially fixed detection path, so that no adjustment is necessary between the microresonator and the detection part.

Figure 4:
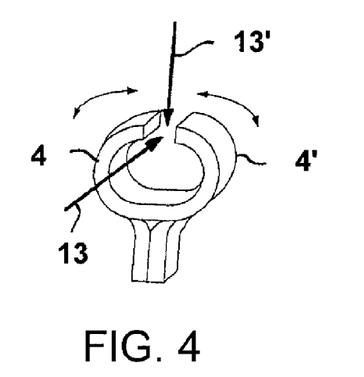
Figure 5:
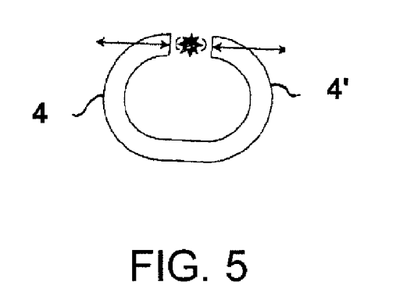

A microresonator with two oscillation arms 4 and 4' is represented in FIG. 4, which may be used in a comparable sensor. There, it is illustrated how a mechanical oscillation of the microresonator, with which the two oscillation arms 4 and 4' oscillate to each other in the manner of a tuning fork, may be optically excited by way of beaming light from two different directions 13 or 13' into an intermediate space between the ends of the two oscillation arms 4 and 4'. FIG. 5 illustrates how, by way of this, with a suitable selection of the wavelength and of a pulse frequency or modulation frequency of the light used for excitation, pressure fluctuations may be produced between the ends of the oscillation arms 4 and 4', which excite the microresonator formed by the oscillation arms 4 and 4' into a mechanical oscillation, depending on the absorption characteristic of the gas surrounding it.

Figure 6:
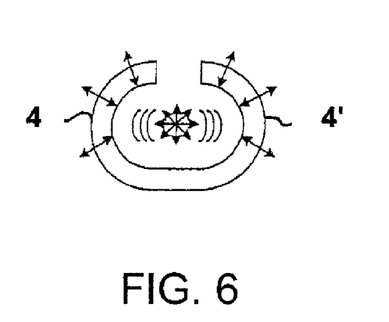

FIG. 6, in a corresponding representation, illustrates an alternative excitation of a mechanical oscillation of a similar microresonator, with which the light for the excitation of the oscillation is not beamed in between the ends of the oscillation arms 4 and 4', but in the middle into a ring formed by the oscillation arms 4 and 4'.

Figure 7:
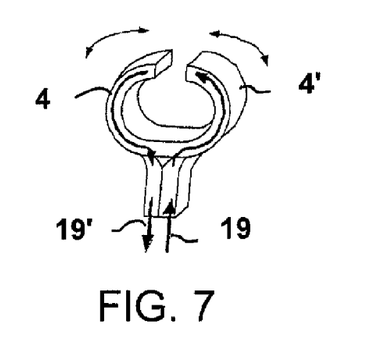

The microresonator from FIG. 4 which is designed either completely or in one of several layers as an optical waveguide, is shown once again in FIG. 7. For detecting the mechanical oscillation of the microresonator, light 14 is fed from a read-out light source which is not shown here, into the microresonator, and this light is reflected at the ends of the oscillation arms 4 and 4' and/or may transmit between the ends of the oscillation arms 4 and 4', so as to be coupled out again for a detection with a light-sensitive element—corresponding to the photodiode 9 from the embodiment examples of FIGS. 1 to 3. An intensity of the light 14', which is coupled out for this, thereby depends on an oscillation of the oscillation arms 4 and 4', by way of which the exiting light 14' is modulated. This modulation may result due to a decrease of the optical coupling between the oscillation arms 4 and 4' with an increasing distance between the ends of these oscillation arms 4 and 4' and/or by way of a change of resonance characteristic of a Fabry-Perot resonator formed between the ends of the oscillation arms 4 and 4', which is caused by way of this.

Figure 8:
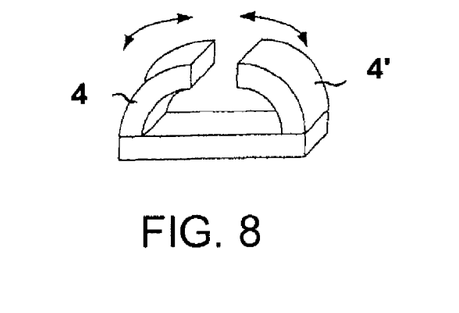
Figure 9:
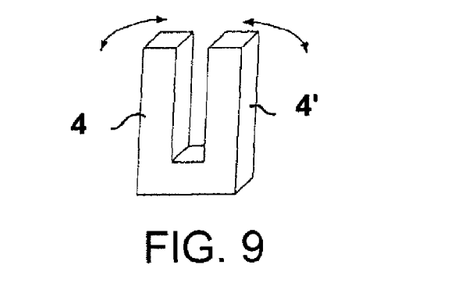
Figure 10:
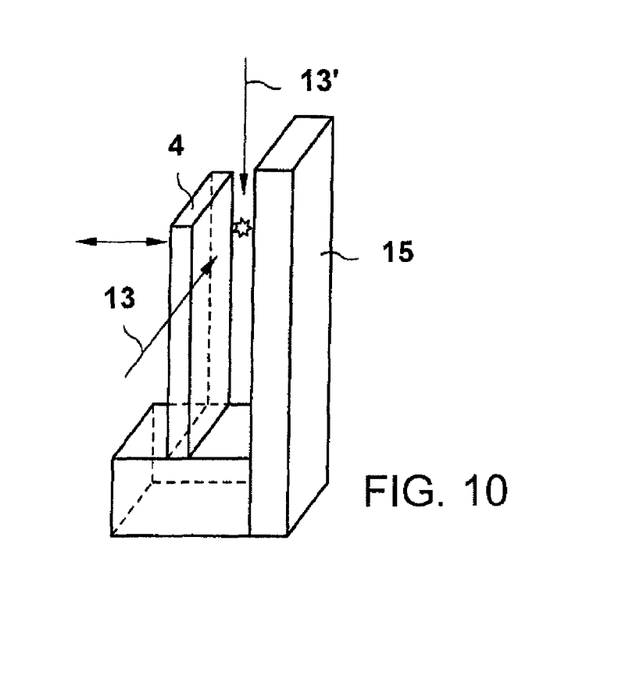

Other embodiments of microresonators, in each case with two oscillation arms 4 and 4' which may be used in similar sensors, so as to be optically excited into a mechanical oscillation which is likewise detected optically, are represented in the FIGS. 8 and 9. A further microresonator which is similar to the microresonator of the embodiment example of FIG. 1 and comprises only one oscillation arm 4, is represented in FIG. 10. There, it is indicated how the oscillation arm 4 of the microresonator may be excited into an oscillation which is to be read out optically, by way of radiating with light of an excitation source, from one of two possible directions 13 and 13', when this light is modulated with a frequency which corresponds to a resonant frequency of the microresonator and has a wavelength which corresponds to an absorption wavelength—possibly also a sub-harmonic or upper-harmonic excitation wavelength—of a gas located in the environment of the oscillation arm 4. In this case, the light of the excitation source is directed onto a space between the oscillation arm 4 and an adjacent fixed wall 15. In order to achieve an as effective as possible opto-acoustic excitation of the mechanical microresonator, one may also design a coupling region between the excitation device and the microprocessor, which is formed between the oscillation arm 4 and the wall 15, such that an excitation pulse by way of reflection at mirror elements, may repeatedly interact with the gas to be examined.

With the sensors suggested here, a change of the optical characteristic of the read-out device is utilised, in order to measure or evaluate a produced oscillation of the microresonator. With some of the suggested embodiments, for this, at least parts of the microresonator, which form a system capable of mechanical oscillation, are designed such that they operate as optical waveguides. The suggested optical detection of the oscillation of the microresonator may thereby be effected in a different manner and utilize different effects, in particular the change of a Fabry-Perot resonator which is formed between ends of the oscillation arms 4 and 4' of the respective microresonator, an intensity change on transmitting light between these ends and a cross-talk of light in the evanescent field between different waveguides 7, 7' and 7". The detection of the mechanical oscillation may thereby be effected in particular by way of an interferometric reading-out.

The suggested sensors are performed as integrated-optical construction, for example based on silicon, which permits a miniaturization of the sensor into chip-based systems. Due to the suggested shape of the microresonators, a high quality of the oscillators formed by them and thus a high detection sensitivity results. One may achieve a decoupling of the sensor from electronic components which may likewise be present as the case may be, by way of the fact that the respective oscillation condition of the microresonator is optically monitored. The construction on a common substrate 1, results in a time-consuming alignment in the sensor head which contains the substrate 1 and the component arranged thereon, not being necessary.

A miniaturization of the suggested sensors is possible by way of their integrated optical type of construction in planar technology. An inexpensive mass production may be realized by way of full-wafer technology.

The optical detection provided for reading out the oscillation may ascertain an amplitude of a deflection of the mechanical microresonator with a submicrometer resolution. Thereby, preferably coherent laser radiation is used for the detection of the oscillation and preferably in the form of single-mode laser signals. Thereby, the highest physically possible resolution may be achieved by way of the use of an amplitude modulation detection or phase modulation detection.

With the suggested sensors, the excitation of a mechanical oscillation of the respective microresonator is effected in an optical or acousto-optical manner, wherein the thus produced oscillation is read out via an oscillation-induced change of a light intensity, wavelength or a phase of a test light beam, in particular amid the use of an evanescent interaction of electromagnetic fields, of optical mode couplings or diffraction effects.

A further possible embodiment envisages an optical coupling of two or more oscillating nano-wires as microresonators. Thereby, the complete sensor element is completely fibre-coupled or waveguide-coupled. The sensor may be designed completely as an integrated-optical element or also in a hybrid arrangement, in which only a part of the sensor forms planar-integrated optics.

A sensor of the suggested type is conceivable as an individual embodiment or also conceivable as a light-guide-coupled sensor system network, in which individual sensors are characterised by different resonant frequencies and/or in which individual sensor elements are read out by way of individual read-out wavelengths or modulation frequencies of a sample light beam.

The sample light beam or read-out beam, which is used for reading out the mechanical oscillation—guided through the light waveguide 5—may be produced by a spectrally narrow-band or in particular in the case of sensor networks, also by a spectrally wide-band light source. The optical a waveguide used in the sensor may be manufactured of mono-crystalline semiconductor material or of another dielectric material. A planar realization of the sensor in SOI technology is typical, with which the oxide layer is etched free in an environment of a microresonator. The preferably optically single-mode waveguides may be designed as rib waveguide or as rib-loaded layer waveguides. The light waveguide which connects the excitation lightwave to the environment of the microresonator may be designed as an integrated-optical-waveguide. Thereby, it is also conceivable for the excitation pulses and the scanning signals to be guided in a single waveguide. Finally, also a light signal used for the excitation may also simultaneously be used for reading out a prevailing oscillation condition of the microresonator. The prevailing oscillation condition of the microresonator may be scanned by way of a beam reflected at the microresonator being effected by way of an integrated-optical Michelson interferometer or an integrated-optical Young interferometer, wherein the waveguide circuit forming the read-out device is preferably realized in single-mode technology. The light waveguide of the excitation device may indeed be multimode.

The applied optical waveguides may in each case be tapered in width at the input or output facets. The mechanical microresonator may finally be brought into a suitable gas resonator or between suitable gas reflectors, such that excitation energy introduced from the excitation light source is converted as effectively as possible into oscillation energy.

What is claimed is:

1. A gas sensor with a mechanical microresonator, comprising:
    an excitation device for an optical excitation of a mechanical oscillation of the microresonator and a read-out device for detecting the oscillation of the microresonator,
    wherein the read-out device comprises a waveguide for optically reading out the oscillation of the microresonator, the waveguide and the microresonator being arranged on a dielectric or semiconducting substrate, wherein the excitation device comprises a light waveguide which is arranged on the same substrate and which optically connects an excitation light source to a direct environment of the microresonator.

2. The gas sensor according to claim 1, wherein the substrate is formed by a semiconductor wafer or a part of a semiconductor wafer.

3. The gas sensor according to claim 1, wherein the substrate is formed from silicon or comprises a silicon layer.

4. The gas sensor according to claim 1, wherein at least one of the microresonator and the light waveguide of the excitation device and the waveguide of the read-out device is arranged in or on a semiconductor layer which is separated from the substrate by a blocking layer which is removed at some locations.

5. The gas sensor according to claim 1, wherein the excitation light source comprises a light-emitting diode serving as an excitation light source.

6. The gas sensor according to claim 1, wherein the excitation light source may be operated in a pulsed or wavelength-modulated or intensity-modulated manner, with a pulse frequency or modulation frequency which corresponds to a resonant frequency of the microresonator.

7. The gas sensor according claim 1, wherein the excitation light source is set up for emitting light of a tunable wavelength.

8. The gas sensor according to claim 1, wherein the microresonator comprises one or two oscillation arms.

9. The gas sensor according to claim 8, wherein the waveguide of the read-out device is arranged close to the oscillation-capable oscillation arm or to at least one of the oscillation arms of the microresonator, such that light exiting from this waveguide, after a reflection at the oscillation arm of the microresonator, may be coupled again into the waveguide.

10. The gas sensor according to claim 8, wherein the waveguide or a further waveguide of the read-out device extends over the oscillation arm or at least one of the oscillation arms of the microresonator.

11. The gas sensor according to claim 1, wherein the waveguide or a further waveguide of the read-out device extends over a first oscillation arm and a second oscillation arm of the microresonator, such that a coupling of light from one end of the first oscillation arm to one end of the second oscillation arm is possible.

12. The gas sensor according to claim 11, wherein the ends of the two oscillation arms comprise parallel, part-reflecting surfaces which form a Fabry-Perot resonator between the two oscillation arms.

13. The gas sensor according to claim 11, wherein the first-mentioned waveguide of the read-out device is optically coupled to the waveguide extending over the oscillation-capable oscillation arms.

14. The gas sensor according to claim 1, wherein the read-out device comprises at least two waveguides which are realized on the same substrate and which are optically coupled to one another, wherein one of the waveguides is optically coupled to the mechanical microresonator, wherein a read-out light source is arranged at one end of one of the waveguides and wherein a light-sensitive element is arranged at another end of one of these waveguides.

15. A method comprising:
    providing a gas sensor with a mechanical microresonator, the gas sensor including an excitation device for an optical excitation of a mechanical oscillation of the microresonator and a read-out device for detecting the oscillation of the microresonator, wherein the read-out device comprises a waveguide for optically reading out the oscillation of the microresonator, the waveguide and the microresonator being arranged on a dielectric or semiconducting substrate, wherein the excitation device comprises a light waveguide which is arranged on the same substrate and which optically connects an excitation light source to a direct environment of the microresonator; and
    analyzing a gas composition with the gas sensor, with which gas located in the environment of the microresonator is radiated with light of the excitation light source, such that the microresonator is exited into an oscillation when a wavelength of this light corresponds to an absorption wavelength of the gas, wherein the oscillation condition is detected by way of the read-out device.

* * * * *